(12) United States Patent
Hughes

(10) Patent No.: US 7,575,765 B1
(45) Date of Patent: Aug. 18, 2009

(54) TOPICAL INSECT REPELLENT

(75) Inventor: Carl C. Hughes, Waynesville, NC (US)

(73) Assignee: Whup-A-Bug, Inc., Waynesville, NC (US)

(*) Notice: Subject to any disclaimer, the term of this patent is extended or adjusted under 35 U.S.C. 154(b) by 0 days.

(21) Appl. No.: 11/956,535

(22) Filed: Dec. 14, 2007

(51) Int. Cl.
*A61K 36/889* (2006.01)
*A61K 36/13* (2006.01)
*A61K 36/00* (2006.01)

(52) U.S. Cl. .................. 424/727; 424/770; 424/725

(58) Field of Classification Search .................. None
See application file for complete search history.

(56) References Cited

U.S. PATENT DOCUMENTS

| | | | |
|---|---|---|---|
| 5,106,622 A | 4/1992 | Sherwood et al. | |
| 5,688,509 A | 11/1997 | Radwan et al. | |
| 5,965,137 A | 10/1999 | Petrus | |
| 6,231,865 B1 | 5/2001 | Hsu et al. | |
| 6,544,530 B1 * | 4/2003 | Friedman | 424/400 |
| 2002/0082279 A1 * | 6/2002 | Schultz | 514/330 |
| 2005/0181001 A1 | 8/2005 | Roentsch et al. | |
| 2006/0008486 A1 * | 1/2006 | Lewis | 424/401 |
| 2006/0165746 A1 | 7/2006 | Markus et al. | |
| 2006/0182775 A1 | 8/2006 | Everett | |
| 2006/0193921 A1 | 8/2006 | Brown et al. | |
| 2007/0134195 A1 * | 6/2007 | Ward et al. | 424/74 |
| 2008/0069785 A1 * | 3/2008 | Jones | 424/59 |

OTHER PUBLICATIONS

Photograph of WHUP-A-BUG® product embodying applicant's previous formulation (specification paragraph [0005]). Originally introduced Feb. 2000 as BUG-OFF, and orginally in Africa. Name changed to WHUP-A-BUG® in Jan. 2003.

* cited by examiner

*Primary Examiner*—Christopher R. Tate
*Assistant Examiner*—Deborah A. Davis
(74) *Attorney, Agent, or Firm*—Carter & Schnedler, P.A.

(57) ABSTRACT

An "all-natural" topical insect repellent formulation having a long shelf life. The formulation includes a carrier base of fractionated coconut oil, and an effective amount of at least one essential oil with insect repellent capabilities. As active ingredients the essential oils cedarwood oil, citronella oil and lemongrass oil may be employed, with a total concentration of these active ingredients of 15.3% by weight.

2 Claims, No Drawings

TOPICAL INSECT REPELLENT

BACKGROUND OF THE INVENTION

The invention relates generally to topical insect repellent or deterrent formulations and, more particularly, to "natural" insect repellent or deterrent formulations which employ essential oils having insect repellent capabilities.

A number of insect repellent and deterrent formulations, particularly for mosquitoes, have previously been developed, including "natural" insect repellents which include essential oils with insect repellent capabilities, as an alternative to chemicals such as the chemical known as DEET (diethyl-m-toluamide). Mosquitoes in particular can transmit a number of serious diseases, such as West Nile virus and encephalitis. Malaria, also transmitted by mosquitoes, remains a public health concern in large parts of the world.

As one example, for several years the inventor herein has marketed an insect repellent under the trademark WHUP-A-BUG®, with a formulation including citronella oil, eucalyptus oil, cedarwood oil, and lemongrass oil in an almond oil base with vitamin E oil as an antioxidant preservative.

SUMMARY OF THE INVENTION

A formulation having a long shelf life and useful as a topical insect repellent is provided, including a carrier base of fractionated coconut oil, and an effective amount of at least one essential oil with insect repellent capabilities.

DETAILED DESCRIPTION

The topical insect repellent formulations disclosed herein have the particular advantage of long shelf life. The present inventor's previous formulation was 3.33% by weight citronella oil, 3.33% eucalyptus oil, 1.67% cedarwood oil, and 3.33% lemongrass oil in a base of almond oil (86.76%) with 1.58% vitamin E oil as a preservative. That previous formulation had a finite shelf life, in the order of eight to twelve months, due to micro-bacterial growth, despite inclusion of the preservative.

Formulations embodying the subject invention employ fractionated coconut oil as a base, which provides greatly extended shelf life. Fractionated coconut oil is a fraction of the whole oil, in which most of the long-chain triglycerides are removed so that only saturated fats remain. It may also be referred to as "caprylic/capric triglyceride" or medium-chain triglyceride (MCT) oil because mostly the medium-chain triglycerides (caprylic and capric acid) are left in the oil. Because it is completely saturated, fractionated oil is even more heat stable than other forms of coconut oil and has a nearly indefinite shelf life.

Formulations embodying the invention additionally include an effective amount of at least one essential oil with insect repellent capabilities. For example, the essential oils cedarwood oil, citronella oil and lemongrass oil may be employed, in concentrations, by weight, of 1.36% to 1.74% cedarwood oil, 3.55% to 3.99% citronella oil and 9.02% to 9.57%% lemongrass oil. Eucalyptus oil as included in the present inventor's previous formulation is not currently included because eucalyptus oil is not on an EPA list of exempt ingredients. As compensation for the non-inclusion of eucalyptus oil, the concentration of lemongrass oil is increased. A particular preferred formulation comprises, by weight, 1.74% cedarwood oil, 3.99% citronella oil, 9.57% lemongrass oil, and 84.7% fractionated coconut oil. The total concentration of the active ingredients cedarwood oil, citronella oil and lemongrass oil is thus a relatively high 15.3% by weight. The shelf life is essentially indefinite.

The formulation disclosed in the paragraph above is effective against mosquitoes, gnats, no-see-ums, flies, fleas and many other insects. The formulation is suitable for both humans, including children, and animals.

The specific gravity of each component makes the formulation process difficult, inasmuch as too much of any individual oil dilutes or overpowers the other individual oils, and accordingly tends to reduce the effectiveness of the other individual oils. Through testing and a number of trials, the concentration of active ingredients in the formulation was increased to 15.3%, while ascertaining that the individual oils are not diluted or diminished in their effectiveness. In other words, the characteristics of the individual oils are maintained.

It is important that the essential oils be balanced into a formula that destroys the cuticle or protective membrane of an insect. In this way, the insect can be repelled and actually killed by prolonged exposure to the product. It is believed that insects avoid scents and substances that will kill them, and accordingly that is why the formulation repels so effectively. It is believed that the insects recognize that they have to leave the area or die. It is the manner in which insects have survived for millions of years.

As noted above, the characteristics of the individual oils are maintained in the disclosed formulation, to the end that a wide range or insects are repelled. As examples, citronella oil repels mosquitoes and gnats. Lemongrass oil repels roaches, ants, wasps and beetles. Cedarwood oil repels ticks, fleas and flies.

Insect repellent formulations embodying the invention accordingly are highly effective, are "all natural," and, in addition, have virtually unlimited shelf life.

While specific embodiments of the invention have been described herein, it is realized that numerous modifications and changes will occur to those skilled in the art. It is therefore to be understood that the appended claims are intended to cover all such modifications and changes as follows in the spirit and scope of the invention.

What is claimed is:

1. A formulation having a long shelf life and useful as a topical insect repellent, consisting essentially of:
    a carrier base of fractionated coconut oil; and
    effective amounts of essential oils with insect repellent capabilities, the essential oils comprising, by weight, cedarwood oil within the range 1.36% to 1.74%, citronella oil within the range 3.55% to 3.99%, and lemongrass oil within the range 9.02% to 9.57%.

2. The formulation of claim 1, which comprises by weight, 1.74% cedarwood oil, 3.99% citronella oil, 9.57% lemongrass oil, and 84.7% fractionated coconut oil.

* * * * *